United States Patent [19]

Hilverda

[11] Patent Number: Plant 7,412

[45] Date of Patent: Jan. 1, 1991

[54] CARNATION NAMED HILTOPPER

[75] Inventor: Jan J. Hilverda, Aalsmeer, Netherlands

[73] Assignee: Hilverda b.v., Aalsmeer, Netherlands

[21] Appl. No.: 308,758

[22] Filed: Feb. 10, 1989

[51] Int. Cl.[5] ..... A01H 5/00

[52] U.S. Cl. ..... Plt./70

[58] Field of Search ..... Plt./70

*Primary Examiner*—James R. Feyrer

*Attorney, Agent, or Firm*—Charles W. Rummler

[57] ABSTRACT

A new spray carnation cultivar particularly distinguished by its continuous blooming habit and profuse production of relatively small flowers having an overall orange coloration and being borne on erect, rigid peduncles emitted alternately from a strong, upright flowering stem having a length of about 60 cm. from a plant having a strong, vigorous, upright growth habit with abundant foliage.

1 Drawing Sheet

BACKGROUND OF THE NE PLANT

My new spray carnation originated as a seedling of a hybrid resulting from my crossing of two unnamed and unpatented carnation varieties selected from my collection of carnation plants maintained at my nursery at Aalsmeer, The Netherlands, for breeding purposes, the object of this crossing being to improve the range of varieties for commercial production by having more rapid growth, better flower colors and improved production rate. This particular seedling was selected by me for propagation because of its dainty orange colored flowers and an apparently vigorous growth habit and propagation of this selected plant was done by me at Aalsmeer by means of cuttings with very satisfactory results. This led me to direct further propagation of this selected seedling through several successive generations at Aalsmeer by means of cuttings, which demonstrated conclusively that this new plant would maintain its distinctive characteristics from generation to generation and that its homogenetic character could be assured for commercial production.

DESCRIPTION OF THE DRAWING

My new spray carnation cultivar is illustrated by the accompanying photographic drawing which shows, in full color, the upper portion of a flowering stem having blooms and buds in several stages of maturity, as well as a face view of the flower, several petals and a bud at the beginning of its opening stage, the colors shown being as nearly true as it is reasonably possible to obtain by conventional photographic procedures.

DESCRIPTION OF THE NEW PLANT

The following is a detailed description of my new spray carnation variety based upon observations made during the current year at Aalsmeer, the color designations being according to The R.H.S. Colour Chart published by The Royal Horticultural Society of London, England.

THE PLANT

Origin: Seedling.

Parentage:

*Seed parent.*—An unnamed and unpatented carnation variety.

*Pollen parent.*—An unnamed and unpatented carnation variety.

Both varieties having been selected by me from my collection of carnation varieties maintained at Aalsmeer for breeding purposes.

Classification:

*Botanic.*—*Dianthus caryophyllus* L.

*Commercial.*—Spray Carnation.

Form: An erect and tall bush.

Height: About 100 cm., in average.

Growth: Vigorous, strong and upright with a rapid growth rate.

Branching character: Alternate.

Foliage:

*Quantity.*—Abundant.

*Leaf size.*—About 9 to 11 cm. in length.

*Leaf shape.*—Elliptic with entire margins.

*Texture.*—Leathery.

*Color.*—Blue Green for both upper and under sides.

*Leaflets.*—None.

*Ribs and Veins.*—The midrib is prominent.

THE BUD

Size: Medium.

*Diameter.*—About 10 mm.

*Length.*—About 20 to 25 mm.

Shape: Cylindrical.

Opening rate: With mature bud, the flower petals appear in about five days.

Color of petals: When sepals first divided, light orange.

When petals begin to unfurl: Orange, shading to brick red.

Sepals:

*Number.*—Six.

*Shape.*—Long ovate with acute apex.

*Character.*—The sepals are hooded over the bud before dividing and stand up as the flower petals unfurl.

*Color.*—Inside: Light green. Outside: Dark Green.

*Striae.*—Little to none, with a light green color.

Calyx:

*Shape.*—Cylindrical.

*Size.*—Medium.

*Splitting.*—The calyx does not split.

*Aspect.*—Smooth.

Flowering stem:

*Length.*—About 60 cm., in average.

*Character.*—Rigid and erect.
*Color.*—Dark Green.

THE FLOWER

Blooming habit: Continuous and profuse.
Flower size: Small.
*Diameter.*—Approximate 50 mm.
*Depth.*—Approximately 25 mm.
Borne: Singly on straight, upright peduncles emitted in longitudinally-spaced relation from a tall, strong and erect flowering stem, there being more than three flower per stem.
Flower shape: When bloom first opens, the flower has a high center. When bloom matures, the flower tends to flatten.
Petalage:
*Number of petals.*—About 58 to 62, in average.
*Arrangement.*—Imbricated.
*Form.*—Fan-shaped with crenate/dentate margins and rounded outer end.
*Texture.*—Soft.
*Appearance.*—Velvety.
*Color.*—All petals: Body — Mars Orange, R.H.S. 31-C. More Pinkish Orange, R.H.S. 35-B/C, toward the center of the flower with irregular reddish flecks, R.H.S. 44-B. Base — Brick red to white.
Flower stem:
*Length.*—Averages about 50 to 60 cm.
*Character.*—Sturdy and upright.
*Color.*—Dark green.
Discoloration after full bloom: None.
Fragrance: Weak.
Persistence: The flowers hang on and dry.

Lasting quality: As a cut flower, ten to fourteen days.

REPRODUCTIVE ORGANS

Stamens:
*Number.*—Four to seven.
*Arrangement.*—Evenly arranged around the ovary.
*Anthers.*—Two to four. Size: Normal. Color: White.
*Filaments.*—Length: About 15 to 20 mm. Color: White.
*Pollen.*—Color: White.
Pistils:
*Number.*—One.
*Style.*—Length: About 15 mm. Color: White.
*Stigma.*—Color: White.

THE FRUIT

Fertility: The fruit is fertile.
Shape: Lozenge-shaped.
Color at Maturity: Yellow/Brown.

This spray carnation variety most nearly resembles the variety 'Orange Tony' (unpatented). My new variety distinguishes from 'Orange Tony', however, by having smaller leaves, more flower buds per stem and a higher flower production.

I claim:

1. The new and distinct spray carnation variety and the parts thereof, substantially as herein shown and described, characterized by its profuse production of relatively small, generally orange flowers carried on a long flowering stem of a tall plant having a strong and vigorous growth habit.

* * * * *

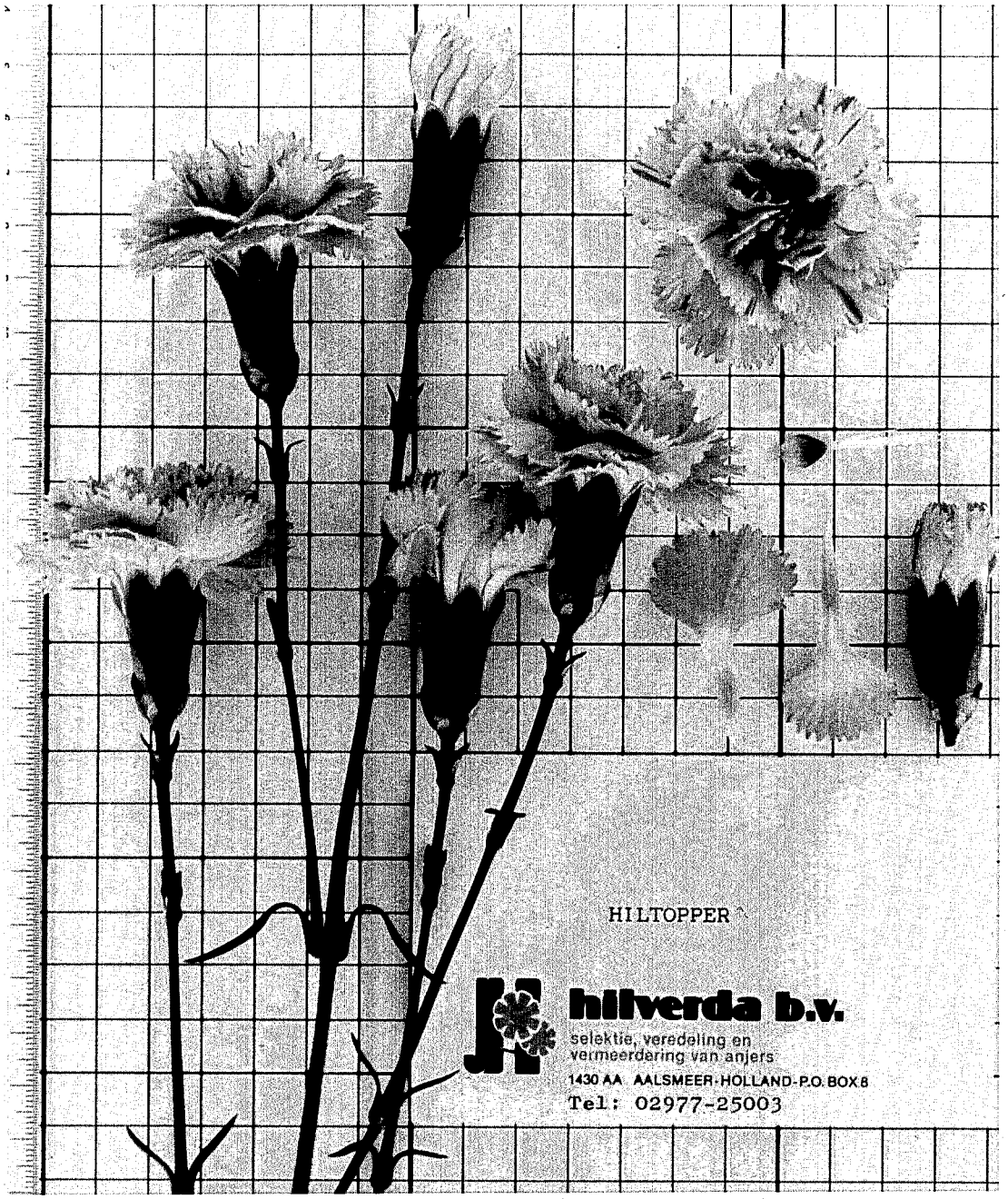
HILTOPPER
hilverda b.v.
selektie, veredeling en
vermeerdering van anjers
1430 AA AALSMEER-HOLLAND-P.O. BOX 8
Tel: 02977-25003